(12) United States Patent
Risi

(10) Patent No.: US 11,484,704 B2
(45) Date of Patent: Nov. 1, 2022

(54) IMPLANTED MEDICAL DEVICES HAVING ELECTRODE ASSEMBLIES

(71) Applicant: Frank Risi, Newton (AU)

(72) Inventor: Frank Risi, Newton (AU)

(73) Assignee: Cochlear Limited, Macquarie University (AU)

(*) Notice: Subject to any disclaimer, the term of this patent is extended or adjusted under 35 U.S.C. 154(b) by 1283 days.

(21) Appl. No.: 14/751,137

(22) Filed: Jun. 26, 2015

(65) Prior Publication Data

US 2016/0022990 A1   Jan. 28, 2016

Related U.S. Application Data

(60) Provisional application No. 62/028,799, filed on Jul. 24, 2014.

(51) Int. Cl.
| | | |
|---|---|---|
| *A61N 1/36* | (2006.01) | |
| *A61N 1/05* | (2006.01) | |
| *A61N 1/372* | (2006.01) | |

(52) U.S. Cl.
CPC ............ *A61N 1/0541* (2013.01); *A61N 1/372* (2013.01)

(58) Field of Classification Search
CPC ........ A61N 1/36125; A61N 1/05; A61N 1/36; A61N 1/375; A61N 1/3752; A61N 1/372; A61N 1/08; A61N 1/37; A61N 1/3968; A61B 5/0031; A61B 2562/0209; A61B 5/0215; A61B 5/042; A61B 5/4836
See application file for complete search history.

(56) References Cited

U.S. PATENT DOCUMENTS

| | | | | |
|---|---|---|---|---|
| 5,571,148 | A | * | 11/1996 | Loeb .................. A61N 1/36036 607/55 |
| 5,810,887 | A | * | 9/1998 | Accorti, Jr. .............. A61N 1/06 607/122 |
| 7,006,875 | B1 | | 2/2006 | Kuzma et al. |
| 7,319,906 | B2 | | 1/2008 | Kuzma et al. |
| 7,587,246 | B2 | | 9/2009 | Hochmair et al. |

(Continued)

FOREIGN PATENT DOCUMENTS

WO   2007/027879 A1   3/2007

OTHER PUBLICATIONS

International Search Report and Written Opinion for PCT/IB2015/054809, dated Mar. 2, 2016.

*Primary Examiner* — Deborah L Malamud
(74) *Attorney, Agent, or Firm* — Piloff Passino & Cosenza LLP; Martin J. Cosenza

(57) ABSTRACT

Disclosed herein are electrode assemblies configured for use with a medical device, such as an implantable medical device. In one aspect, the disclosed electrode assembly includes at least a first electrode and a second electrode, each of which is configured to deliver electrical stimuli to a body part of a recipient. The electrode assembly also includes a first wire that is attached at one end to the first electrode and comprises a conductor that has a first diameter, and a second wire that is attached to the second electrode and comprises a conductor that has a second diameter, with the first diameter being greater than the second diameter. Additionally, each of the first wire and the second wire pass through a proximal end of the assembly is configured to connect the one of the electrodes to a stimulation unit of a medical device.

21 Claims, 6 Drawing Sheets

(56) References Cited

U.S. PATENT DOCUMENTS

| | | |
|---|---|---|
| 8,244,366 B2 | 8/2012 | Chang et al. |
| 8,340,759 B2 * | 12/2012 | McIntyre ................ A61N 1/05 607/2 |
| 2003/0009095 A1 | 1/2003 | Skarda |
| 2007/0135885 A1 | 6/2007 | Risi |
| 2007/0225784 A1 | 9/2007 | Bly et al. |
| 2007/0282411 A1 | 12/2007 | Franz et al. |
| 2009/0005836 A1 | 1/2009 | Chang et al. |
| 2009/0088651 A1 | 4/2009 | Shuros et al. |
| 2012/0221088 A1 | 8/2012 | Thenuwara et al. |

* cited by examiner

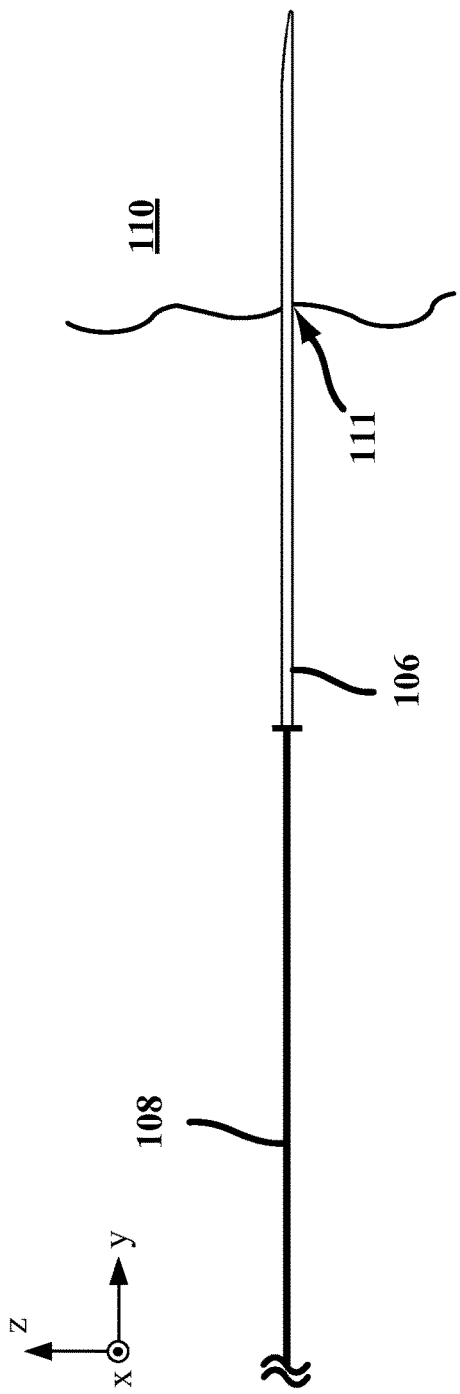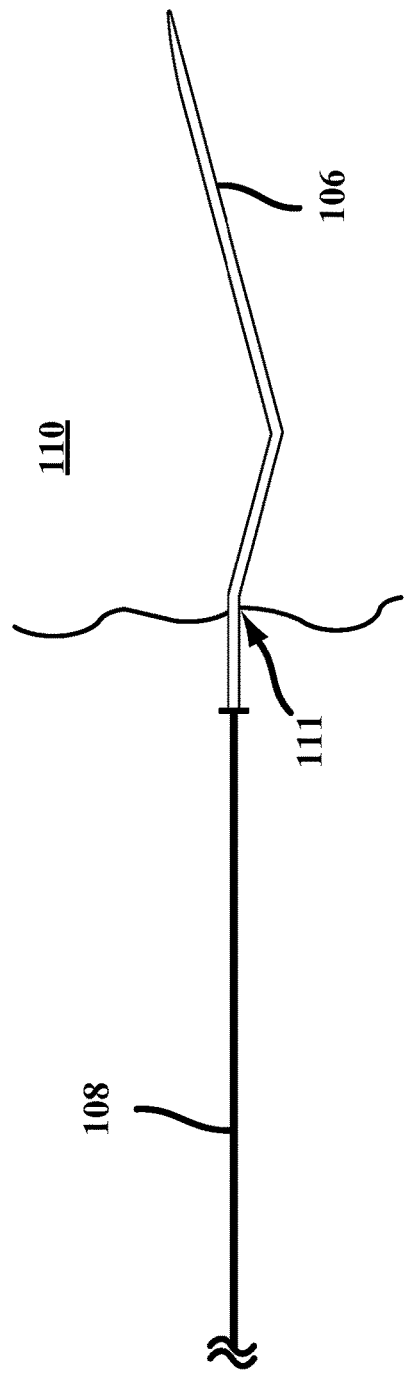
FIG. 1D
FIG. 1E

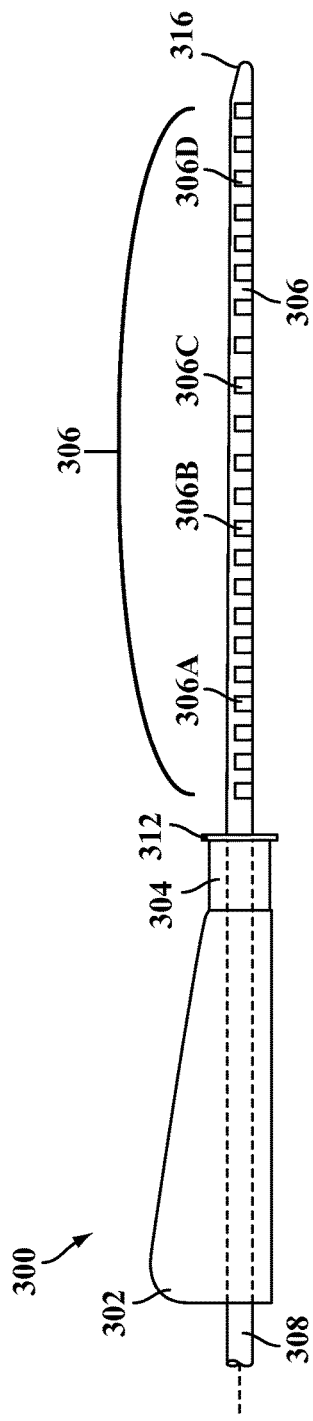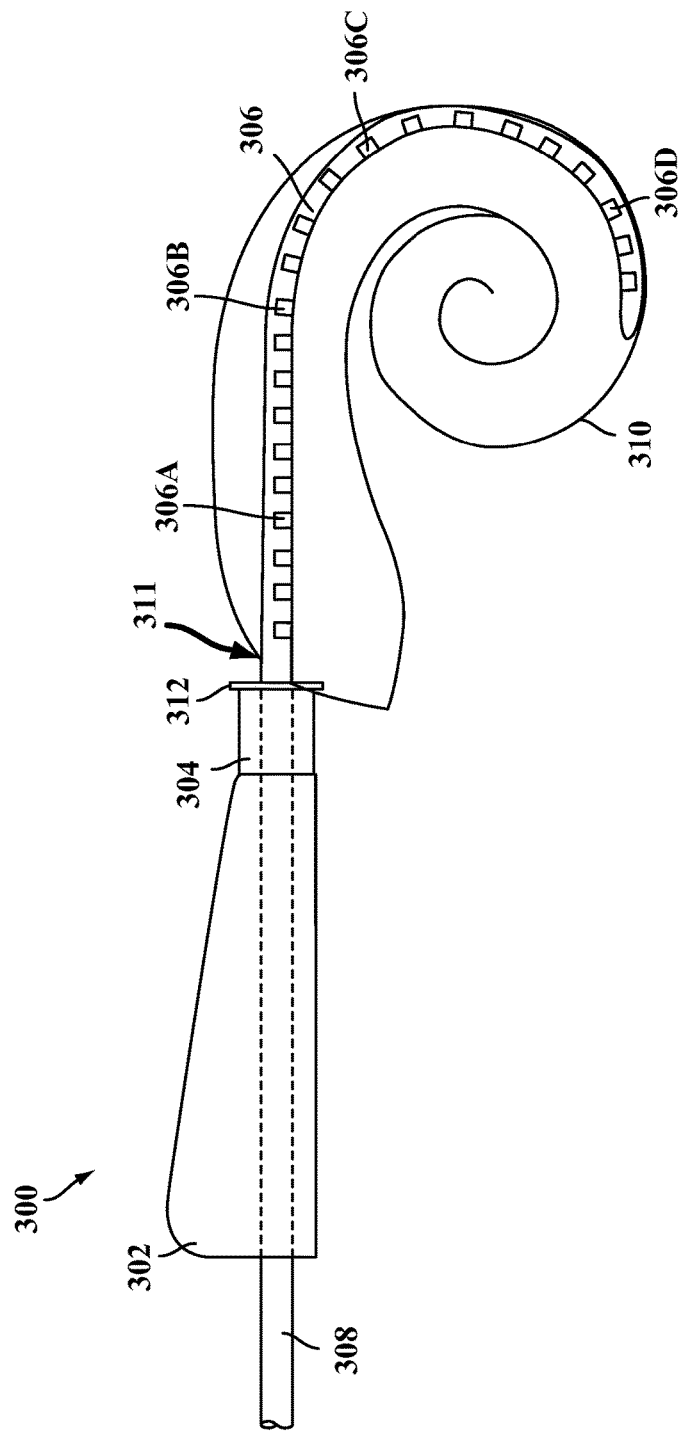
FIG. 3A
FIG. 3B

IMPLANTED MEDICAL DEVICES HAVING ELECTRODE ASSEMBLIES

CROSS-REFERENCE TO RELATED APPLICATION

Priority is claimed to U.S. Provisional Patent Application No. 62/028,799 filed on Jul. 24, 2014, the contents of which are incorporated by reference.

BACKGROUND

Individuals with certain medical conditions may benefit from the use of a medical device. For example, individuals who suffer from certain types of hearing loss may benefit from the use of a hearing prosthesis. Depending on the type and the severity of the hearing loss, a recipient can employ a hearing prosthesis to assist the recipient in perceiving at least a portion of a sound.

A partially implantable medical device typically includes a processing unit that performs at least some processing functions and a stimulation unit that at least delivers a stimulus to a target body part. In the case of a hearing prosthesis, the target body part is often in an auditory pathway of the recipient. The auditory pathway includes a cochlea, an auditory nerve, a region of the recipient's brain, or any other body part that contributes to the perception of sound. In the case of a totally implantable medical device, the implanted component includes both processing and stimulation components.

A surgeon implants the stimulation unit in the recipient, typically inserting into the target body part or otherwise placing on or near the target body part a component configured to deliver the stimulus. If the implantable medical device is a cochlear implant, for example, the surgeon inserts an electrode assembly, which includes one or more electrodes, into the cochlea. The amount of force the surgeon uses to fully insert the component could, depending on the location and the physiology of the target body part, cause the component to buckle and/or deform, thereby rendering a portion of the medical device, if not the entire medical device, inoperable. Consequently, the component should have sufficient stiffness to minimize or prevent buckling and/or deformation in susceptible regions of the device during insertion or implantation.

SUMMARY

The present disclosure provides an improved electrode assembly configured for use in a medical device. In particular, the disclosure relates to a medical device that is configured to deliver electrical stimuli to a recipient and is at least partially implantable in the recipient. An example of such a device is a cochlear implant in which an electrode assembly is surgically inserted into a recipient's cochlea and functions to electrically stimulate regions of the cochlea in order to assist the recipient in perceiving sound.

In one aspect, the disclosed electrode assembly includes at least a first electrode and a second electrode, each of which is configured to deliver electrical stimuli to a body part of a recipient. The electrode assembly also includes a first wire that is attached at one end to the first electrode and comprises a conductor that has a first diameter, and a second wire that is attached to the second electrode and comprises a conductor that has a second diameter, with the first diameter being greater than the second diameter. The first wire passes through a proximal end of the assembly and is configured to connect the first electrode to a stimulation unit of a medical device. Similarly, the second wire passes through the proximal end of the assembly and is configured to connect the second electrode to the stimulation unit.

In another aspect, a medical device comprises a processing unit configured to generate stimulation signals, a stimulation unit configured to generate electrical signals based on the stimulation signal, an electrode assembly comprising a plurality of electrodes, and a plurality of wires configured to connect the plurality of electrodes to the stimulation unit. The stimulation unit is configured to be implanted in a recipient, as is the electrode assembly, which is configured to be inserted into a body part of the recipient. The electrodes are configured to stimulate the body part. Additionally, two or more wires in the plurality of wires have different diameters.

Advantageously, because larger diameter wires are generally stiffer than smaller-diameter wires, the wire configurations of the electrode assembly describe in each aspect may result in a requisite amount of stiffness in a proximal end of the electrode assembly so as to minimize a likelihood of the electrode assembly buckling and/or deforming during insertion. Additionally, providing the requisite stiffness with the wires can help to reduce the size of, or obviate the need for, an additional stiffening member in the electrode assembly. And for an electrode assembly in which the stiffening member would otherwise be made of an expensive metal, such as platinum or a platinum alloy, the wire configurations can also help to reduce the manufacturing and retail costs of the medical device.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

FIGS. 1D and 1E show an electrode assembly at different points during an insertion procedure, according to an example.

FIG. 3A is a pre-insertion side view of an example assembly configured for use with the implantable medical device of FIG. 1.

FIG. 3B is a post-insertion side view of the example assembly depicted in FIG. 3A.

DETAILED DESCRIPTION

The present device will be described herein principally with respect to a medical device of the type comprising a processing unit, a stimulation unit, and an electrode assembly, the latter of which includes an electrode array surgically inserted into a body part of a recipient.

Figure 1A:
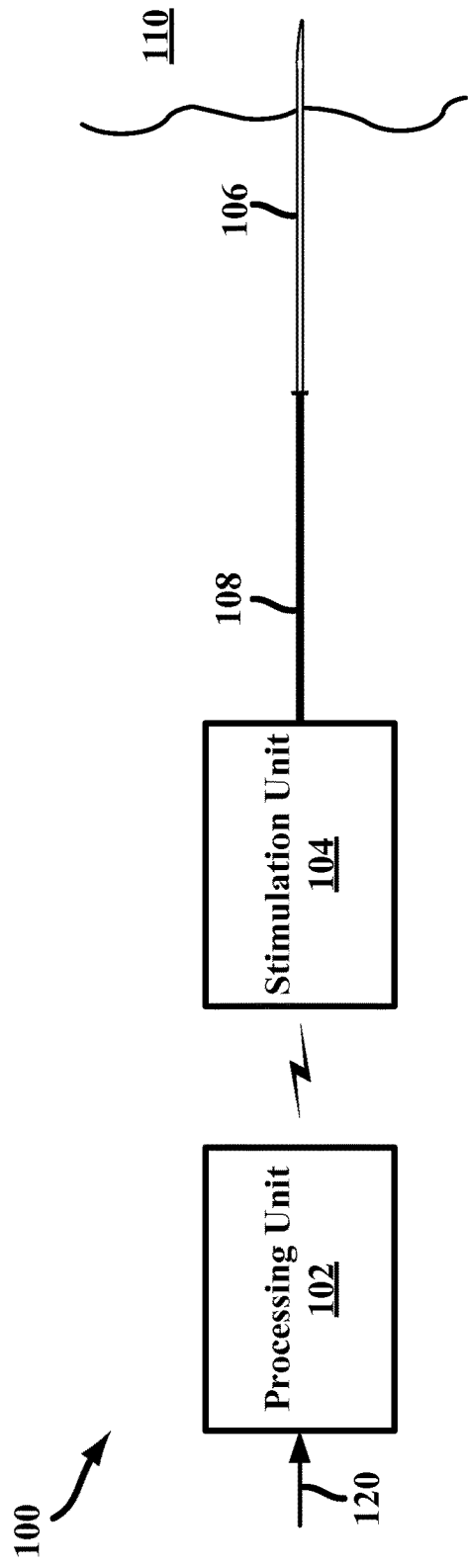
FIG. 1A is a diagram of a medical device, according to an embodiment.

Referring to the drawings, as noted above, FIG. 1A is a diagram of a medical device 100 that includes a processing unit 102, a stimulation unit 104, and an electrode assembly 106. A plurality of wires included in a cable 108 connects the stimulation unit 104 to the electrode assembly 106. In an example arrangement, the recipient wears the processing unit 102 on the recipient's body, while the stimulation unit 104, the electrode assembly 106, and the cable 108 are implanted in the recipient's body. More specifically, in the example arrangement, the electrode assembly 106 is inserted into a body part 110 of the recipient. Further, the electrode assembly 106 includes one or more electrodes, each of which is configured to deliver electrical stimuli to a recipient's body part 110.

In an example implementation, the processing unit 102 receives a signal 120 from an environment. The origin of the signal 120 depends on the purpose of the medical device 100. For instance, if the medical device 100 is a cochlear implant, the signal 120 is a sound, perhaps received via a microphone. As another example, if the medical device 100 is a deep brain stimulator, the signal 120 may be indicative of a detected chemical and/or electrical signal in the recipient's brain.

The processing unit 102 processes the signal 120 to generate stimulation signals and sends the stimulation signals to the stimulation unit 104 via a transcutaneous link (i.e., wireless link through the recipient's skin) or a percutaneous link (i.e., a wired link through the recipient's skin) The stimulation unit 104, in turn, receives the stimulation signals, responsively generates electrical signals, and sends the electrical signals to the electrode assembly 106 via the plurality of wires in the cable 108. Note that in some examples, the stimulation unit 104 may perform some, or perhaps even all, of the functions of the processing unit 102.

Figure 1B:
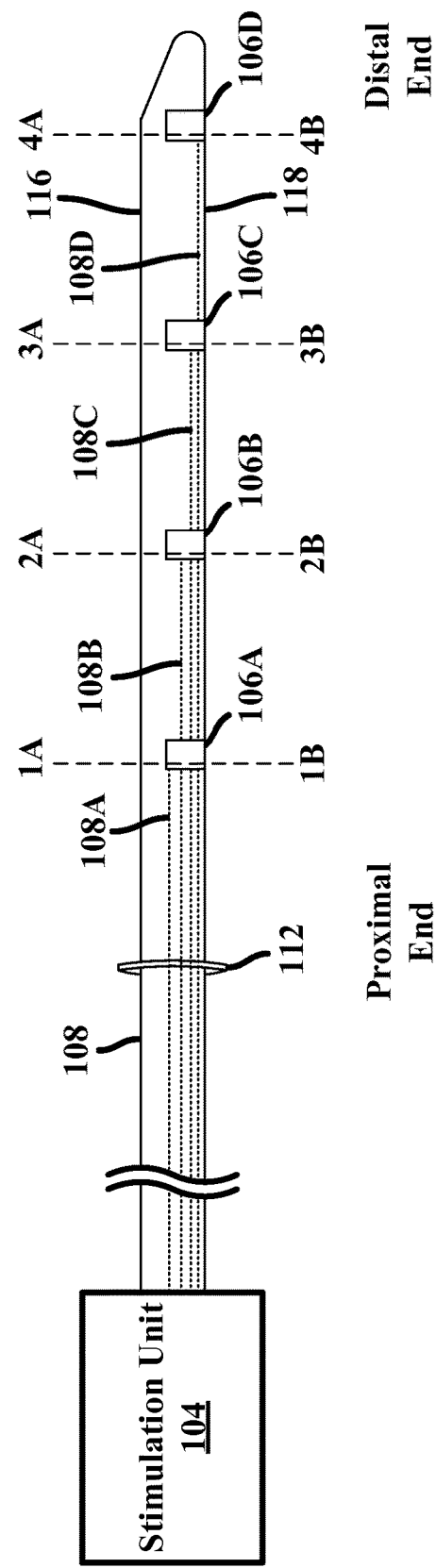
FIG. 1B is a side view of an electrode assembly and a cable depicted in FIG. 1A, according to an embodiment.

In practice, each electrical signal causes one electrode, or possibly more than one electrode, mounted on or in the electrode assembly 106 to stimulate a specific region of the body part 110. FIG. 1B is a side view of components of the electrode assembly 106 and the cable 108. In one example, the electrode assembly 106 and the cable 108 interface at a band 112, which also acts to prevent the electrode assembly 106 from being inserted beyond a predetermined depth or to form a seal at the insertion point on the body part 110.

The electrode assembly 106 includes four electrodes: a first electrode 106A, a second electrode 106B, a third electrode 106C, and a fourth electrode 106D. In practice, however, the electrode assembly 106 may include more or fewer than four electrodes, perhaps as many as twenty-two electrodes or more. The first electrode 106A is closest to a proximal end of the electrode assembly 106 (i.e., the end of the assembly that is at an insertion point on the body part 110), and the second electrode 106B, the third electrode 106C, and the fourth electrode 106D are progressively closer to a distal end of the electrode assembly 106 (i.e., the end of the electrode assembly 106 inserted the farthest into the body part 110).

A type of electrode included in the electrode assembly 106 depends on a particular application or a therapeutic objective of the medical device 100. For instance, the electrode assembly 106 may include half-band electrodes disposed on or near a medial surface 116 of the electrode assembly 106 (i.e., a surface facing toward a center of the body part 110). Alternatively, the electrode assembly 106 may include half-band electrodes disposed on or near a lateral surface 118 of the electrode assembly 106 (i.e., a surface facing away from the center of the body part 110). Or the electrode assembly 106 may include banded electrodes that extend substantially around the electrode assembly 106. Further, the electrode assembly 106 may include any electrode now known or later developed that is suitable for the application or the therapeutic objective of the medical device 100.

Each of the one or more electrodes 106A-106D is manufactured from a biocompatible conductive material, such as, for example, platinum. In other examples, the one or more electrodes may include an additional or an alternative biocompatible conductive material. Further, the one or more electrodes may be coated with a biocompatible covering that does not substantially interfere with the delivery of the stimuli 108 to the body part 110.

As also shown in FIG. 1B, the cable 108 includes wires 108A, 108B, 108C, and 108D, each of which comprises the same conductor, such as platinum iridium, and has the same or a substantially similar diameter (e.g., within a tolerance of +/−5%). Each of the wires 108A-108D connects a respective electrode 106A-106D to the stimulation unit 104. While the example depicted in FIG. 1B shows each of the electrodes 106A-106D connected to the stimulation unit 104 by a single wire, two or more wires connect each of the electrodes 106A-106D to the stimulation unit 104 in other examples.

Figure 1C:
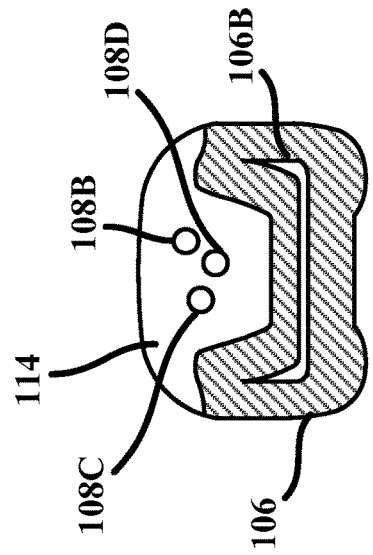
FIG. 1C shows cross-sections of the electrode assembly depicted in FIG. 1B, according to an embodiment.
Figure 1C:
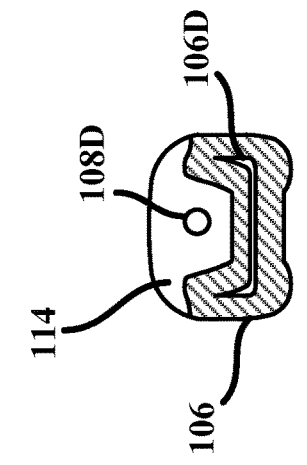
Figure 1C:
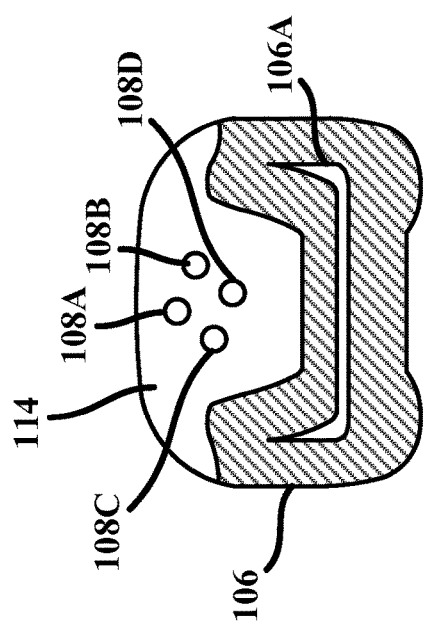
Figure 1C:
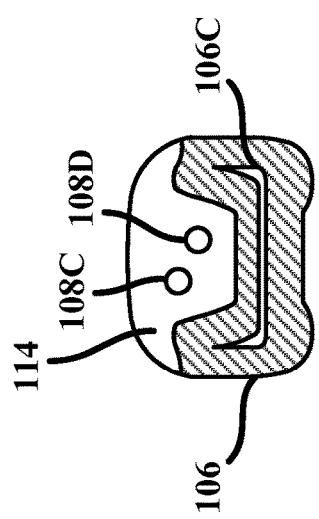

The wires 108A-108D are depicted in FIG. 1B to illustrate the relative uniformity in the size of their respective diameters. As an example of a practical arrangement of the wires 108A-108D in the electrode assembly 106, FIG. 1C depicts cross-section views of the electrode assembly at each of four locations on the electrode assembly 106, as indicated by the reference lines 1A-1B, 2A-2B, 3A-3B, and 4A-4B in FIG. 1B. As shown in FIG. 1C, the wires 108A-108D are arranged in a volumetric core 114 of the electrode assembly 106. In another example, the wires 108A-108 are arranged in a different configuration that is suitable for the electrode assembly 106.

FIGS. 1D and 1E show the electrode assembly 106 at two different points during an insertion procedure. As shown in FIG. 1D, a surgeon inserts the electrode assembly into the body part 110 at an insertion point 111. In order to fully insert the electrode assembly 106, the surgeon applies a force in a longitudinal direction (as indicated by the y-axis in FIG. 1D). However, depending on the physiology of the body part 110, in general or for a given recipient, the force applied by the surgeon to overcome an internal resistance of the body part 110 may cause the electrode assembly to buckle or become deformed in a region near the proximal end of the electrode assembly 106, such as a region between the band 112 and either the first electrode 106A or the second electrode 106B. The electrode array 106 may buckle or become deformed in a transverse plane (as indicated by the z-axis), as shown in FIG. 1E, and/or in a lateral plane (as indicated by the x-axis going into/out of the plane of the paper). Additionally, depending on the amount of force applied in the lateral plane and/or transverse plane during the insertion procedure, the electrode assembly 106 could also buckle or become deformed prior to the insertion point 111.

Buckling and/or deformation can limit the operability of one or more of the electrodes 106A-106D, thereby reducing the effectiveness of the medical device 100. In fact, the damage to the electrode assembly 106 may, in some situations, be severe enough to render the medical device 100 inoperable.

In accordance with the present disclosure, varying the thickness of the wires 108A-108D may provide the requisite amount of stiffness near the proximal end of the electrode array 106, thereby minimizing or preventing buckling/deformation near the proximal end of the electrode assembly 106. FIGS. 2A-2D show side views of example wire configurations of an electrode assembly. For illustrative purposes, the wire configurations depicted in FIGS. 2A-2D are described with respect to the medical device 100. It should be understood, however, that the described wire configurations may be adapted for use in other medical devices. Additionally, while the wire configurations depicted in FIGS. 2A-2D depict one wire connected to each of the electrodes 106A-106D, one or more additional wires may be also connected to each of the electrodes 106A-106D.

Figure 2A:
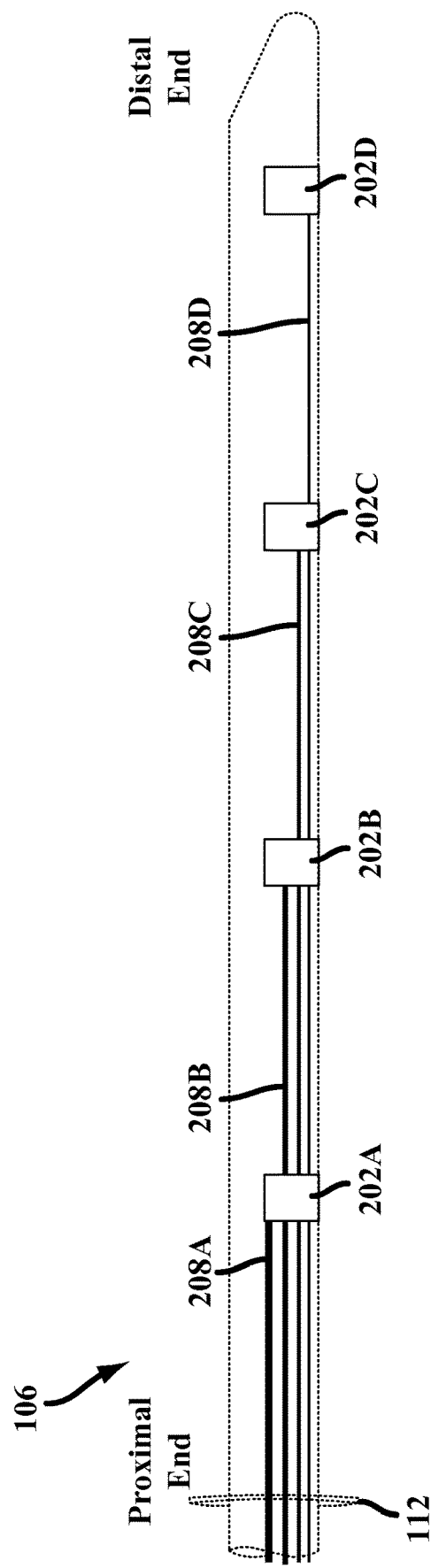
FIGS. 2A, 2B, 2C, and 2D are side views of example wire configurations for connecting a stimulation unit of the implantable medical device to one or more electrodes.

In each of the example wire configurations depicted in FIGS. 2A-2D, at least one wire has different diameter (e.g., a different gauge or thickness, exclusive of an insulating material) that the other wires. By way of example, FIG. 2A shows a first wire configuration that includes a first wire 208A, a second wire 208B, a third wire 208C, and a fourth wire 208D. In this example, each of the wires 208A-208D has a different diameter: the first wire 208A has the largest diameter, the second wire 208B has the second largest diameter, the third wire 208C has the third largest diameter, and the fourth wire 208D has the smallest diameter. The collective thickness of the wires 208A-208D may provide the electrode assembly 106 with a stiffness between the band 112 and the first electrode 106A, or even the second electrode 106B that is sufficient to minimize the risk of, or prevent, damaging one or more of the electrodes 106A-106D during the insertion process. Additionally, because the diameter of the wires 106B-106D are progressively smaller, the electrode assembly 106 may have the requisite flexibility to conform to the shape of the body part during or shortly after insertion. That is, the thickness of smaller diameter wires does not appreciably impact the flexibility of the electrode assembly between the distal end and, as one example, the second electrode 106B.

Figure 2B:
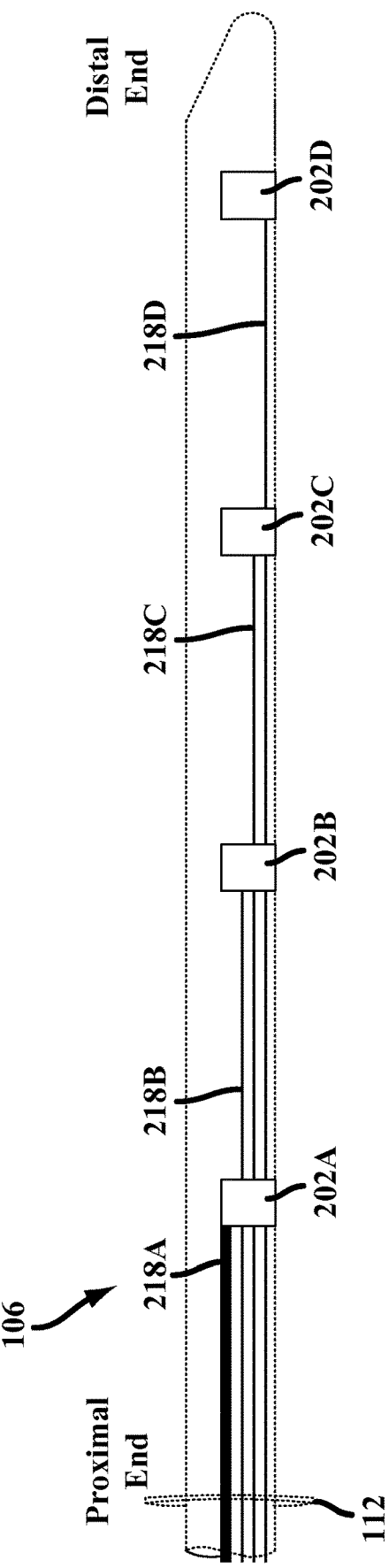

As another example, FIG. 2B shows a second wire configuration that includes a first wire 218A, a second wire 218B, a third wire 218C, and a fourth wire 218D. In this example, the second wire 218B, the third wire 218C, and the fourth wire 218D have the same diameters or substantially similar diameters (e.g., within a tolerance of +/−5%). To provide the requisite stiffness at the proximal end of the electrode assembly 106, the diameter of the first wire 218A is larger than the diameter of the other wires 218B-218D. Moreover, the first wire 218A may have a larger diameter than the diameter of the first wire 208A depicted in FIG. 2A.

In the examples described with respect to FIGS. 2A and 2B, the diameters of the wires may provide sufficient stiffness at the proximal end of the electrode assembly 106 to obviate the need to include an additional stiffening member in the electrode assembly 106. In some examples, however, the electrode assembly 106 may include a stiffening member.

Figure 2C:
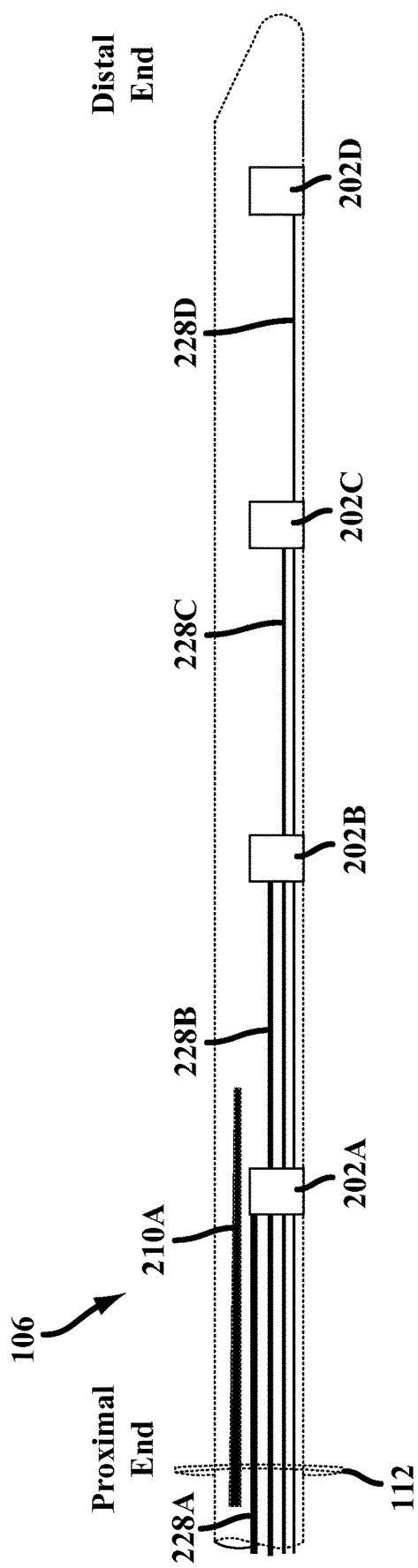

By way of example, FIG. 2C shows a third wire configuration that includes a first wire 228A, a second wire 228B, a third wire 228C, and a fourth wire 228D. As in FIG. 2A, the diameter of the wires 228A-228D decreases from the first wire 228A to the fourth wire 228D.

In FIG. 2C, the electrode assembly 106 also includes a stiffening member 210A. The stiffening member 210A provides additional stiffness near the proximal end of the electrode assembly 106, e.g., from a region between the first electrode 106A and the second electrode 106B to a region near the base 204. Including the stiffening member 210A in the electrode assembly 106 may allow for smaller-diameter wires 228A-228D. Comparing the wire configuration shown in FIGS. 2A and 2C, for example, the first wire 228A may have a smaller diameter than the first wire 208A, the second wire 228B may have a smaller diameter than the second wire 208B, etc.

Figure 2D:
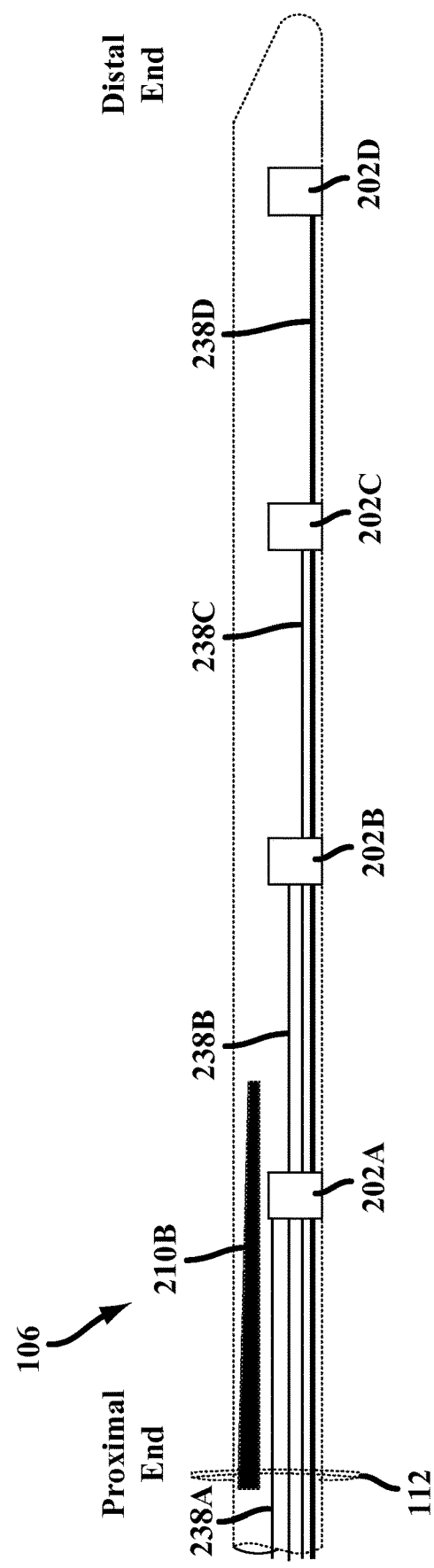

As yet another example, FIG. 2D shows a fourth wire configuration that includes a first wire 238A, a second wire 238B, a third wire 238C, and a fourth wire 238D. In the fourth wire configuration, the first wire 238A, the second wire 238B, and the third wire 238C have the same or substantially similar diameters (e.g., within a tolerance of +/−5%). The fourth wire 238D has a greater diameter than the other wires, thereby providing additional stiffness in at least a portion of the proximal end of the electrode assembly 106, e.g., the region between the first electrode 106A and the base 204.

Additionally, the electrode assembly 106 in FIG. 2D includes a stiffening member 210B, which provides additional stiffness near the proximal end of the electrode assembly 106. Alternatively, the electrode assembly 106 may not include the stiffening member 210B, in which case the fourth wire 238D would have a larger diameter than depicted in FIG. 2D in order to provide the requisite stiffness at the proximal end of the electrode assembly 106.

In FIGS. 2C and 2D, the stiffening members 210A and 210B extend longitudinally from a region near the band 112 to a region between the first electrode 106A and the second electrode 106B. Alternatively, depending on the application of the medical device 100, the stiffening members 210A and 210B may be longer or shorter than depicted in FIGS. 2C and 2D, respectively. A length of the stiffening members 210A and 210B may correspond to a distance from the insertion point in the body part 110 to a first turn in the lateral wall of the cochlea 310. In other examples, the stiffening members 210A and 210B may be longer or shorter, depending upon the application of the electrode assembly 106.

In one aspect, a thickness of the stiffening members 210A and 210B is inversely proportional to collective thickness of the wires connecting the electrodes 106A-106D to the stimulation unit 104. Thus, having wires with larger diameters may allow for a thinner stiffening member, thereby reducing the cost of the stiffening member and/or the electrode assembly 106.

The stiffening members 210A and 210B may be formed of any metallic or non-metallic material suitable for inclusion in the electrode assembly 106, such as platinum. The stiffening members 210A and 210B may also be annealed prior to being inserted into the electrode assembly 106 in order to increase toughness and reduce brittleness. Alternatively, the stiffening member 210A may by formed of a plastic, or perhaps even of glass.

To provide the requisite stiffness at different points along the electrode assembly 106, the stiffening members 210A and 210B may taper toward their respective distal ends. In another example, the stiffening members 210A and 210B each have a uniform thickness, or even a different shape.

Other characteristics of the wires described with respect to FIG. 2A-2D may also affect the stiffness of the electrode assembly 106. For example, for a given wire configuration one or more of the wires may comprise a non-annealed conductor, thereby providing additional stiffness, while one or more other wires may comprise an annealed conductor.

As another example, one or more of the wires may comprise different conductors. For instance, one or more wires may comprise a platinum iridium conductor, while one or more other wires comprise a different conductor, such as copper. Or each of the wires may comprise the same alloy conductor but have different percentages of the alloy components in order to provide the requisite stiffness. For instance, if each of the wires comprises a platinum iridium conductor, one or more wires may comprise an alloy with a greater percentage of iridium than one or more other wires. In some examples, the conductors of larger-diameters wires may have a greater percentage of the alloy component than the conductors of smaller-diameter wires, while in other examples the conductors of smaller-diameter wires have a greater percentage of the alloy component than the conductors of larger-diameter wires. That is, depending on the amount of proximal stiffness needed for a given application of the medical device 100, the percentage of stiffening alloy components may be proportional or inversely proportional to the diameter of the wires.

The insulator used for the wires may also affect the stiffness of the electrode assembly 106. By way of example, the thickness of the insulator around the wires may vary in order to provide additional stiffness. As another example, different polymers may be used to insulate the wires, with at least one polymer providing additional stiffness. Thus, in addition to at least one wire having a different diameter or thickness than the other wires, the insulator for one or more of the wires may have a different thickness and/or comprise a stiffer polymer than one or more other wires.

As an additional example, FIGS. 3A and 3B show side views of an insertion assembly 300 configured to insert an electrode assembly into a body part. More specifically, FIG. 3A shows a pre-insertion side view of the insertion assembly 300, and FIG. 3B shows a post-insertion side view of the electrode assembly 300 in the body part, which is a cochlea 310.

The insertion assembly 300 is one example of an assembly that a surgeon may use to insert a component of an medical device into a body part of a recipient. The insertion assembly 300 includes a holding member 302, a collar member 304, an electrode assembly 306, a cable 308, and a band 312. The electrode assembly 306 is one example the electrode array 106 described with respect to FIGS. 2A-2D. Additionally, the cable 308 and the band 312 are the same as or are substantially similar to the cable 108 and the band 112.

The electrode assembly 306 has a profiled tip 316 at the distal end and interfaces with the collar member 304 at the band 312. The profiled tip 316 may include any structure, shape, or configuration of a tip that is now known or later developed and is suitable for use with the electrode assembly 306. During the insertion process, the profiled tip 316 guides the electrode assembly 306 into the cochlea 310 and reduces friction during the insertion process.

The electrode assembly 306 also includes an electrode array 302 comprising one or more electrodes, including a first electrode 306A, a second electrode 306B, a third electrode 306C, and a fourth electrode 306D, which are the same as or substantially similar to the electrodes 106A-106 described with respect to FIGS. 2A-2D. In FIGS. 3A and 3B, the electrode array 302 includes twenty-two electrodes. In other examples, the electrode array 302 may include more or fewer than twenty-two electrodes. Moreover, the electrode array 302 may be a linear array or a nonlinear array.

The surgeon prepares the cochlea 310 by performing a cochleostomy. During the insertion process, the surgeon grips the holding member 302, and possibly the collar member 304 as well, and inserts the electrode assembly 306 into an insertion point 311 near the basal region of the cochlea 310. As the surgeon inserts the electrode assembly 306 into the cochlea 310, the electrode assembly 306 flexes to conform to the shape of the cochlea 310. The wires in the electrode assembly 306, which are arranged in one of the wire configurations shown in FIGS. 2A-2D, provides sufficient stiffness near the proximal end of the electrode assembly 306 (e.g., in a region between the band 312 and the first electrode 306A) to minimize or prevent damage to the electrode assembly 306 during the insertion process.

Once the surgeon has inserted the electrode assembly 306 into the cochlea 310, surgeon may then connect the cable 308 to the stimulation unit 104, if not already connected, and perform any remaining implantation procedures. In some examples, the surgeon may detach or otherwise remove the collar member 304 and/or the holding member 312 prior to performing any remaining implantation procedures.

Although certain components of the medical device 100 are described as being external to the recipient and other components are described as being implanted within the recipient, it should be understood that variations are possible. For instance, the processing unit 102 and the stimulation unit 104 may be completely implanted in a recipient, perhaps in a single hermetically-sealed enclosure. Alternatively, an external device or external devices may include the processing unit 102 and the stimulation unit 104.

It should also be understood that the specific configurations shown in the figures are merely representative of numerous possible configurations now known or later developed and that variations are therefore possible. For instance, certain components or combinations of components can be combined, distributed, re-positioned, re-ordered, omitted, added, or otherwise modified.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. An assembly comprising:
   a first electrode and a second electrode, wherein each electrode is configured to deliver electrical stimuli to a body part of a recipient;
   a first wire attached at one end to the first electrode and comprising a first conductor that has a first diameter, wherein the first wire passes through a proximal end of the assembly and is configured to connect the first electrode to a stimulation unit of a medical device; and
   a second wire attached to the second electrode and comprising a second conductor that has a second diameter, wherein the second wire passes through the proximal end of the assembly and is configured to connect the second electrode to the stimulation unit, and wherein the first diameter is greater than the second diameter, wherein
   the assembly is configured to be inserted into the recipient.

2. The assembly of claim 1, further comprising a biocompatible band at the proximal end of the assembly, wherein at least one of the first wire or the second wire provides, in a region of the electrode assembly between the biocompatible band and at least one of the first electrode or the second electrode, a stiffness that minimizes a likelihood of the assembly buckling or deforming when the assembly is inserted into the body part.

3. The assembly of claim 1, wherein the first electrode is positioned closer to the proximal end of the assembly than the second electrode.

4. The assembly of claim 3, further comprising:
the stimulation unit, wherein the first wire passing through the proximal end of the assembly is connected to and in signal communication with the stimulation unit, and the second wire passing through the proximal end of the assembly is connected to and in signal communication with the stimulation unit.

5. The assembly of claim 1, wherein the second electrode is positioned closer to the proximal end of the assembly than the first electrode.

6. The assembly of claim 1, wherein the first conductor and the second conductor are different conductors.

7. The assembly of claim 1, wherein each of the first conductor and the second conductor comprise an alloy component, and wherein a percentage of the alloy component in the first conductor differs from a percentage of the alloy component in the second conductor.

8. The assembly of claim 7, wherein the percentage of the alloy component in the first conductor is greater than the percentage of the alloy component in the conductor of the second conductor.

9. The assembly of claim 7, wherein the percentage of the alloy component in the second conductor is greater than the percentage of the alloy component in the first conductor.

10. The assembly of claim 9, wherein the percentage of the alloy component in the second conductor results in a greater proximal stiffness than that in the first conductor.

11. The assembly of claim 7, wherein each of the first conductor and the second conductor is platinum iridium, and wherein the alloy component is iridium.

12. The assembly of claim 1, further comprising:
a third electrode configured to deliver electrical stimuli to the body part; and
a third wire attached to the third electrode and comprising a third conductor that has a third diameter, wherein the third wire passes through the proximal end of the assembly and is configured to connect the third electrode to the stimulation unit, and wherein the third diameter differs from at least one of the first diameter and the second diameter.

13. The assembly of claim 12, wherein the third diameter is substantially equal to either the first diameter or the second diameter.

14. The assembly of claim 12, wherein the third electrode is located closer to the proximal end of the assembly than the first electrode and the second electrode, and wherein the third diameter is greater than the first diameter and the second diameter.

15. The assembly of claim 1, wherein the assembly is a cochlear electrode array configured for insertion into a cochlea, wherein the electrode array is connected to a cable leading from the electrode array.

16. A medical device comprising:
a processing unit configured to generate stimulation signals;
a stimulation unit configured to generate electrical signals based on the stimulation signals, wherein the stimulation unit is configured to be implanted in a recipient;
an electrode assembly comprising a plurality of electrodes, wherein the electrode assembly is configured to be inserted into the recipient, and wherein the electrodes are configured to stimulate a body part of the recipient in response to the electrical signals; and
a plurality of wires configured to connect the plurality of electrodes to the stimulation unit, wherein two or more wires have different diameters.

17. The medical device of claim 16, wherein each wire in the plurality of wires has a different diameter.

18. The medical device of claim 17, wherein the medical device is a cochlear implant, and wherein there are at least four electrodes and the plurality of wires include at least four wires connected to respective electrodes, the stimulation unit is a stimulation unit of a cochlear implant.

19. The medical device of claim 16, wherein the two or more wires comprise a first wire and one or more additional wires, and wherein
the first wire has a first diameter,
each of the one or more additional wires has a second diameter, and
the first diameter is greater than the second diameter.

20. The medical device of claim 16, wherein at least two wires in the plurality of wires comprise conductors made of a metal alloy, and wherein a percentage of an alloy component in one of the at least two wires differs from a percentage of the alloy component in another of the at least two wires.

21. The medical device of claim 16, wherein the electrode assembly is a cochlear electrode array configured for insertion into a cochlea, and the plurality of wires are part of the electrode array, the medical device further comprising a cable connecting the stimulation unit to the electrode array, the wires extending through the cable from the electrode array to the stimulation unit.

* * * * *